(12) United States Patent
Kaiser et al.

(10) Patent No.: US 6,370,221 B2
(45) Date of Patent: Apr. 9, 2002

(54) METHOD OF SETTING A POSITION OF AN OBJECT OF MEASUREMENT IN LAYER THICKNESS MEASUREMENT BY X-RAY FLUORESCENCE

(75) Inventors: Karl-Heinz Kaiser, Böblingen; Volker Rössiger, Sindelfingen, both of (DE)

(73) Assignee: Helmut Fischer GmbH Institut fur Elektronik und Messtechnik (DE)

( * ) Notice: Subject to any disclaimer, the term of this patent is extended or adjusted under 35 U.S.C. 154(b) by 0 days.

(21) Appl. No.: 09/812,476

(22) Filed: Mar. 19, 2001

(30) Foreign Application Priority Data

Mar. 17, 2000 (DE) .......................................... 100 13 048

(51) Int. Cl.[7] ............................................ G01N 23/223
(52) U.S. Cl. ............................ 378/45; 378/44; 378/206; 378/150
(58) Field of Search ............................ 378/44, 45, 50, 378/205, 206, 147, 150

(56) References Cited

U.S. PATENT DOCUMENTS 4,590,658 A * 5/1986 Funyu et al. .................. 29/464
4,860,329 A * 8/1989 Weiser et al. .................. 378/50
6,038,280 A * 3/2000 Rossiger et al. .............. 378/50

* cited by examiner

*Primary Examiner*—Robert H. Kim
*Assistant Examiner*—Jurie Yun (57) ABSTRACT

The invention relates to a method of setting a position of an object of measurement in layer thickness measurement by X-ray fluorescence in which a beam of an optical recording device is projected into the beam of the X-radiation and in which the surface of the object of measurement is recorded and output as an image comprising a number of image points, with the distance between the surface and the collimator being changed by an absolute amount of a path of movement, with changes in brightness of the image points being recorded in at least one measuring plane during the at least one change of the distance between the surface and the collimator, with the maximum of the difference in brightness of the image points of an image being ascertained after the at least one change of the absolute amount of the distance, and with the distance between the collimator and the object of measurement being set to the position of the ascertained maximum of the difference in brightness.

23 Claims, 4 Drawing Sheets

METHOD OF SETTING A POSITION OF AN OBJECT OF MEASUREMENT IN LAYER THICKNESS MEASUREMENT BY X-RAY FLUORESCENCE

The invention relates to a method of setting a position of an object of measurement in layer thickness measurement by X-ray fluorescence according to the precharacterizing clause of claim 1.

Setting the correct position of the object of measurement with respect to the primary X-radiation and with respect to the detector is crucial for the correctness of the measurement when measuring thin layers or multiple layers. For such layer analysis, an X-ray fluorescence radiation of individual elements of a specimen is detected and converted into layer thickness(es) and composition(s). Apparatuses which have an X-ray tube in a housing which is substantially opaque to X-rays are used, with emergence of an X-ray beam being provided through an opening. The extent of the X-radiation is restricted to a specific surface area of the specimen by a collimator. In this surface area, an object of measurement is positioned at a defined distance from the collimator on a table which is movable with respect to the measuring head, comprises an X-ray tube, collimator and the other components required here. The measuring head has, furthermore, a proportional counting tube or a detector, which serves for recording the fluorescence radiation of the irradiated area of the surface.

The distance between the collimator and the surface of the object of measurement has to be set to a specific distance or exact measurement, in order that the fluorescence radiation can be recorded with sufficient intensity.

DE 40 03 757 discloses an adjustment in which the collimator itself is used directly as part of the adjustment. In this case, it is provided that the tip of the collimator is moved against the specimen, with the collimator yielding correspondingly on account of a resilient suspension. Subsequently, further relative movement between the specimen and apparatus is stopped and the device draws the collimator away from the specimen again. The distance between the collimator and the specimen can be set by the amount of spring deflection of the collimator. This apparatus has the disadvantage that damage to the surface can occur. In addition, there are inaccuracies in the setting of the distance on account of production inaccuracies and the paths to be moved along, with a cumulative effect of the errors occurring.

A brochure from the company Veeco Instruments Inc., 1997 edition, likewise discloses an apparatus for measuring thin layers by X-ray fluorescence analysis. In this case it is provided that a beam of an optical recording device is projected into the beam of the X-radiation, in order to be able to view the object of measurement. In the case of this method, a laser beam is used for setting the critical distance for the reproducibility of the measurements. This laser beam falls obliquely on the surface of the object of measurement. During upward and downward movement of the object of measurement, the point of impingement of the laser beam shifts for example from right to left on the surface. Cross wires are superimposed in the recording device and are adjusted to the X-ray beam. As soon as the laser of the laser beam projected onto the surface of the object of measurement coincides with the cross wires, the exact working distance is set. This upward and downward movement of thd object of measurement in relation to the measuring head can be performed manually by an operator, with considerable deviations in the said setting being obtained in these measurement results.

Furthermore, this brochure discloses an automatic laser focusing which is intended to increase the reproducibility of the exact setting. This automatic laser focusing method of setting the measuring distance with respect to a surface of an object of measurement has the disadvantage that the surface impinged is only indistinctly visible in the case of highly reflective surfaces, which leads to an inaccurate height setting. The finite size and unsharpness of the specimen surface impinged by the laser leads to setting errors. Furthermore, an additional laser and corresponding shielding are required.

It is also disadvantageous in the case of both methods mentioned that tilting of the specimen surface cannot be recorded.

The invention is therefore based on the object of providing a method of setting a point of impingement of an X-radiation on an object of measurement defined by a distance of a collimator from the surface of the object of measurement which, on its own, makes an exact setting of this distance possible.

This object is achieved according to the invention by the features of claim 1. The steps provided according to the invention for carrying out the method allow an automatic setting of the surface of an object of measurement at a defined distance from the collimator to take place, with a high degree of accuracy of reproduction being obtained for the position of the surface of the object of measurement with respect to the collimator. In addition, additional sources of error can be eliminated by recording the changes in brightness of the image points of an image, as is the case for example with laser focusing with regard to the point of impingement. Furthermore, the accuracy of reproduction in comparison with manual focusing can also be significantly improved. By evaluating the changes in brightness of the image points during the changing of the distance between the surface of the object of measurement and the collimator, automatic setting can take place without additional apparatus. For this purpose, the electronic recording device, which has a beam projected into the beam of the X-radiation, is used in order that the exact setting of the distance between the collimator and the object of measurement is carried out. By ascertaining the maximum difference in brightness of the image points of the images recorded, a fixed, defined distance of the surface of the object of measurement from the collimator can be set. The beam of the electronic recording device is advantageously adjusted in such a way that the focal point lies in a measuring plane which is at the exact distance from the collimator. When a maximum difference in brightness is ascertained, it can be ensured that a sharp image is recorded by the recording device, and that, as a result, the defined distance has been set. The advantageous assignment of the change in brightness of the image points in a measuring plane to a Z coordinate makes it possible that, after ascertaining a maximum difference in brightness of the image points of an image while moving over the path, an exact setting of the distance can be carried out by positioning the surface of the object of measurement and the collimator with respect to each other.

The object of the invention is similarly achieved by an alternative method according to the features of claim 2. The recording of the differences in brightness of the image points of at least one measuring plane and the ascertainment of the maximum take place in analogy with the method according to claim 1. As a difference from the latter, an assignment of the image in a measuring plane to a Z coordinate is not envisaged. The maximum difference in brightness of the image points of an image is advantageously ascertained and the distance between the surface and the collimator is changed once more, a change in direction being envisaged here. During the changing of this distance, the difference in brightness of the image points of an image in respective measuring planes in turn approaches the maximum. As soon as a comparison establishes that the current maximum coincides with the maximum ascertained when the distance was changed the first time, the changing of the distance is interrupted, whereby a focusing of the image and consequently a defined distance of a collimator from the surface of the object of measurement is set.

According to an advantageous refinement of the invention, it is provided that individual measurements for ascertaining changes in brightness of the image points of an image are carried out during a changing of the distance between the collimator and the surface and the individual measurements are carried out at freely preselectable intervals in time or virtually continuously. As a result, the amount of information to be processed, on the one hand, and the speed of the changes in the absolute amount of a preferably freely settable preselectable path, on the other hand, can be determined.

According to a further advantageous refinement of the invention, it is provided that, for ascertaining the maximum value of the difference in brightness in a measuring plane within a path, the image points $y_1$ to $y_N$ are determined in a differential method according to the function $F=\Sigma(y_i-y_{right\ neighbour})^2+\Sigma(y_i-y_{upper\ neighbour})^2$, where $y_i$ is the brightness value of the image points used. As a result, the difference in brightness between a right neighbour and an upper neighbour can be ascertained, so that the entire information of the image points is recorded when the difference in brightness is formed. This ascertained function value is evaluated for the comparison with other function values ascertained by individual measurements.

According to an advantageous refinement of the invention, it is provided that the changing of the distance between the collimator and the surface of the object of measurement corresponds to a path in which at least the exact distance between the collimator and the surface of the object of measurement is passed through. On account of the advantageous setting of the beam of the electronic recording device, the focal point of which lies in the surface of the object of measurement which corresponds to the exact distance of the collimator from the surface of the object of measurement, it is made possible that a first unsharpness, for example above, and a further unsharpness of the focal point, for example below the surface of the object of measurement, is obtained, whereby the maximum of the difference in brightness lying at the focal point can be ascertained with certainty.

According to a further advantageous refinement of the invention, it is provided that the individual measurement is ascertained from a number of individual images at a time interval, and that an average value is formed from the values of the individual images. As a result, possible disturbing influences such as noise on account of divergent values can be minimized.

According to a further advantageous refinement of the invention, it is provided that the changing of the distance is retained during the individual measurement. As a result, changing takes place without any jerks or jolts, whereby the quality can at the same time be increased for the recording of the changes in brightness of the image points. Furthermore, depending on the time intervals, real-time recording can take place for the individual measurement.

According to a further advantageous refinement of the invention, it is provided that the changing of the distance in the approximate search for a maximum of the differences in brightness is carried out at an increased speed. As a result, an approximate position of the exact distance to be set between the collimator and the surface of the object of measurement can be ascertained in first approximation.

According to a further advantageous refinement of the method, it is provided that, for a precision search, the distance between the collimator and the surface of the object of measurement is reset after carrying out the approximate search to a second starting point at a resetting speed. This resetting speed is advantageously greater than the speed of the approximate search, so that rapid carrying out of the setting is made possible.

According to a further advantageous refinement of the method, it is provided that the precision search is carried out at a reduced speed in comparison with the approximate search. This can make it possible for the individual measurements for ascertaining the function value F to be carried out in much closer steps. After carrying out the precision search, the maximum is ascertained by calculating the zero crossing of the first derivative as an approximation by interpolation. Due to possibly image-typical uncertainties, such as for example noise, several maximums may formally occur, but are prevented by smoothing.

According to a further advantageous refinement of the method according to claim 1, it is provided that, after the precision search, the maximum of the approximate search and of the precision search are compared with each other and a path of movement by which the distance between the collimator and the surface is changed by during the precision search after passing through the maximum is calculated. As a result, after the precision search, a direct setting of the correct distance can be obtained.

According to a further advantageous refinement of the method according to claim 1, it is provided that, before the commencement of the approximate search, a preset distance between the collimator and the surface of the object of measurement is increased by an absolute amount. In this way it can be ensured that, in the subsequent approximate search, a maximum is passed through with a high degree of certainty, it being observed during the increase in the distance whether the difference in brightness decreases. As a result, it can be established at the same time that the starting point for carrying out a measurement lies below the focal point of the exact distance in order to permit a reliable setting thereafter. If the differences in brightness were to increase, the process would be stopped and an indication given to the user that another position is being preselected in order to carry out the setting.

According to a further advantageous refinement of the method according to claims 1 and 2, it is provided that the image points ascertained for recording the difference in brightness in an image are recorded separately in individual fields. This makes it possible for the orientation of the surface of the object of measurement to be ascertained by comparison of the individual fields with one another. The positionally correct orientation is of significance in particular in multiple layer measurements and in the measurement of very thick layers. Recording the orientation of the specimen surface makes it possible to compensate for inaccuracies from an ideal orthogonal orientation of the measuring plane with respect to the X-ray beam.

For this, it is advantageously provided that the value of the maximum change in brightness is recorded in every field. As a result, a comparison between the individual fields can be made possible. If, for example, two fields neighbouring each other have the same change in brightness, it can be concluded from this that this area has no difference in height. If a number of fields have an approximately equal value of a change in brightness, it is ascertained that the planar surface of the object of measurement has a positionally correct orientation, in other words is positioned orthogonally with respect to the X-ray beam.

According to a further advantageous refinement of the invention, it is provided that at least a division into four fields is chosen and, for the characterization of a tilting, the coefficient from a right-hand pair of individual fields and a left-hand pair of individual fields and the coefficient from an upper pair and a lower pair of individual fields are formed. This characterizes the tilting or orientation of the surface of the object of measurement. It is advantageously provided that the sum of the squared coefficients is compared with a constant which is a measure of the orthogonality of the surface with respect to the X-ray beam. Depending on the constant, the tolerance can be pre-formed such that it is greater or smaller.

According to a further advantageous refinement of the invention, it is provided that the differences in brightness within each field are recorded and compared with the neighbouring fields and the orientation is ascertained, a table with an inclination correction being activated in an XY plane with respect to the collimator. This can make possible an adjustment of the orientation of the surface deviating from the ideal plane with respect to the X-ray beam.

Further advantageous embodiments are specified in the further claims.

Particularly preferred embodiments of the method are described in more detail with reference to the following drawings, in which.

Figure 1:
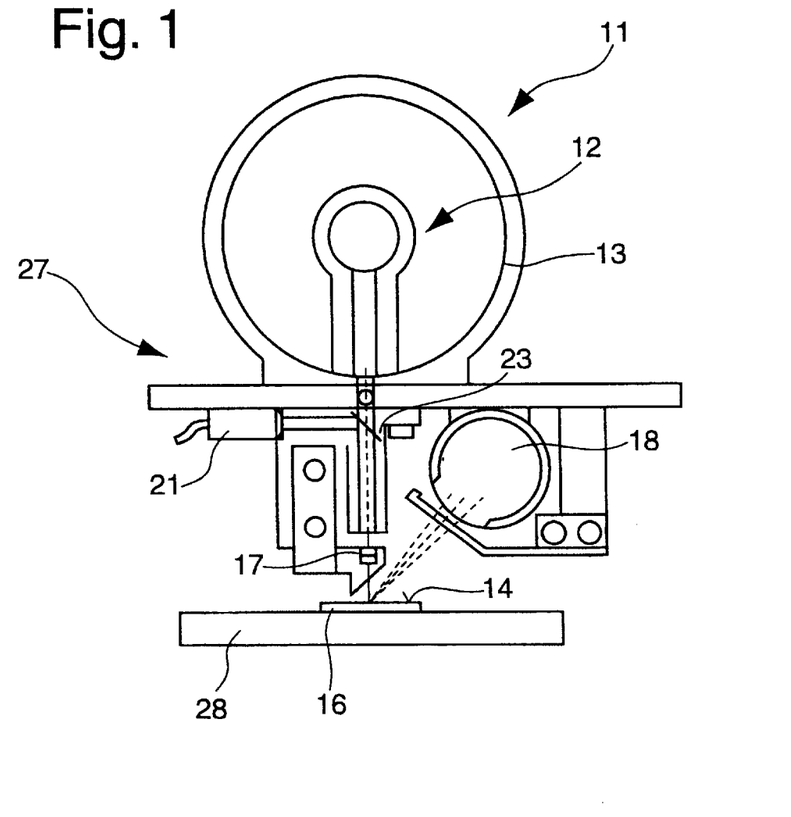
FIG. 1 shows a schematic view of an apparatus for measuring thin layers by X-radiation.

Represented in FIG. 1 is an apparatus 11 for measuring thin Layers or for layer thickness analysis by X-radiation, in particular by X-ray fluorescence radiation. Such an apparatus 11 has an X-ray tube 12 for generating X-rays in a housing 13. An X-ray beam leaves via an opening in the housing 13 and impinges on a surface 14 of an object of measurement 16. A specific surface area of the X-radiation is restricted on the surface 14 of the object of measurement 16 by a collimator 17 arranged at a defined distance 26 from the surface 14. The fluorescence radiation emitted by the irradiated specimen is recorded and evaluated by a proportional counting tube 18 or some other detector.

The apparatus 11 has an electronic display device 21, the beam 22 of which is projected into the beam of the X-radiation via a semi-transparent mirror 23 and is directed onto a surface 14 of the object of measurement 16. This display device 21 allows the image of the surface 14 to be reproduced on a monitor (not represented in any more detail).

For the accuracy of the layer thickness measurement it is necessary that an exact distance 26 between the surface 14 of the object of measurement 16 and the collimator 17 is set, determining the point of impingement of an X-radiation on an object. This distance 26 is fixed on one occasion on an apparatus. It is subsequently necessary for this distance 26 to be repeatedly set exactly. One reason for this is that a specific position of the proportional counting tube 18 for recording the secondary radiation being emitted is necessary in order to record a minimum intensity of the radiation. The components, such as for example the tube 12, housing 13, collimator 17, proportional counting tube 18, form a measuring head 27. The object of measurement 16 is arranged with respect to the said measuring head on a table 28 which is movable in three dimensions. The following embodiments are described on the basis of a fixed measuring head 27 and a movable table 28, in particular in the Z coordinate, in other words reducing or increasing the distance 26. It goes without saying that the table 28 may similarly be fixedly arranged and the measuring head 27 variable with respect to it, or that both the measuring head 27 and the table 28 may be moved with respect to each other, or that part of the movement of the table 28, part of the movement of the measuring head 27 or some other variable pattern of movements may be envisaged.

Figure 2:
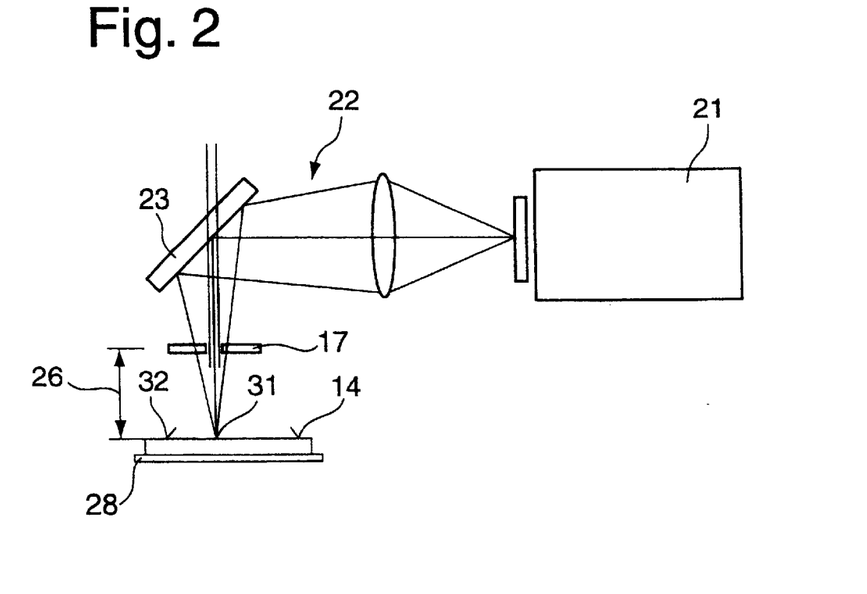
FIG. 2 shows a schematic view of a beam of an electronic display device, the focal point of which lies in a surface of an object of measurement.

The beam 22 from the electrical display device 21 to the surface 14 is represented in FIG. 2. In this setting, a focal point 31 lies in a measuring plane 32, which in this position corresponds to the surface 14. The display device 21 ascertains a sharp image of the surface 14. In this position of the surface 14, an exact position of the distance 26 between the collimator 17 and the surface 14 is also obtained. Consequently, the exact working distance 26 with the greatest possible focusing is obtained.

The image recorded by the display device 21 is read out in individual pixels. This may take place for example by means of a CCD camera chip, it being possible for signals digitized via a Frame-Crapper card to be transferred to a graphics card, which can take place without processor support.

Figure 3:
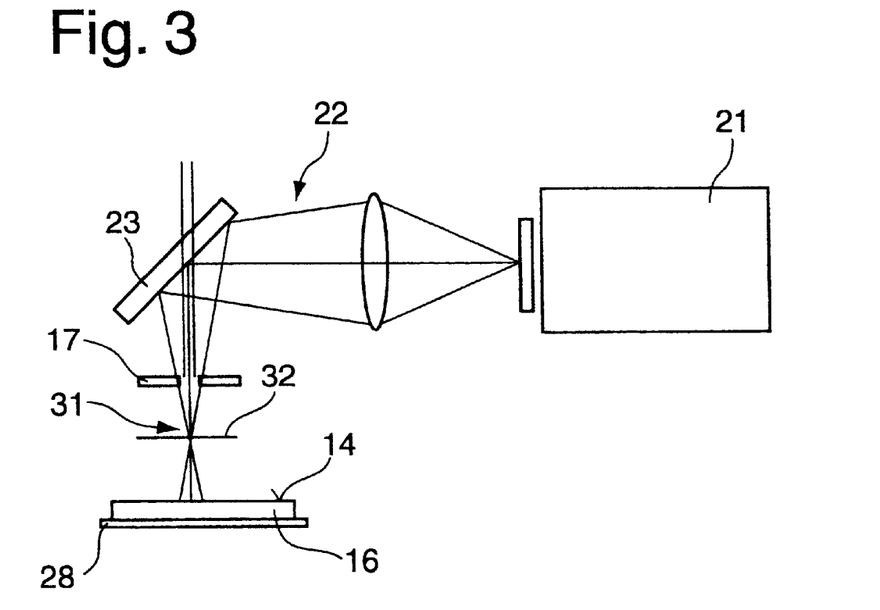
FIG. 3 shows a schematic representation according to FIG. 2, in which the focal point lies above the surface.
Figure 4:
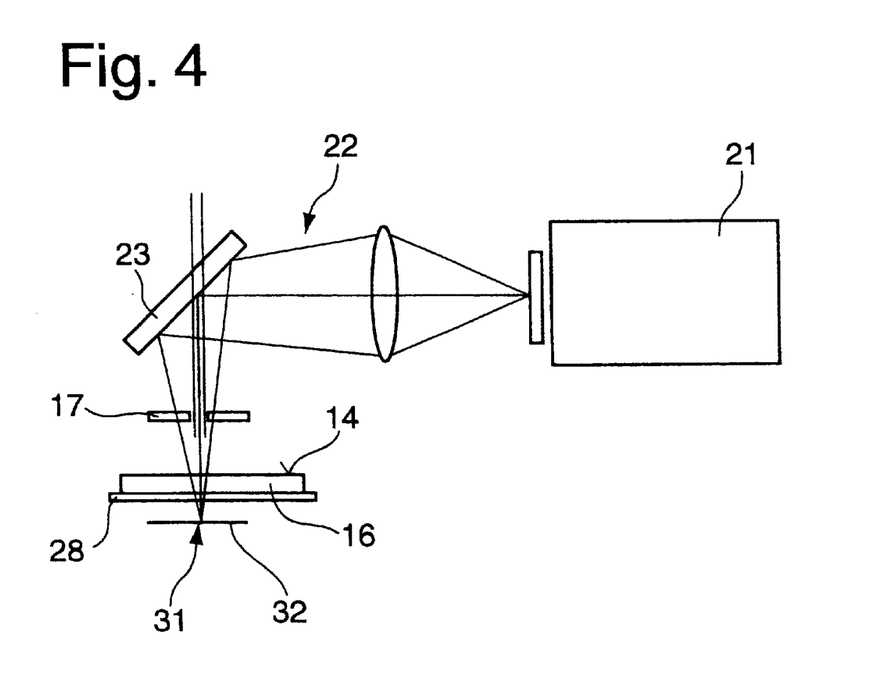
FIG. 4 shows a schematic representation according to FIG. 2, in which the focal point lies below the surface.

Depending on the position of the surface 14, the measuring plane 32 formed by the focal point 31 may lie above the surface 14, as is represented for example in FIG. 3, or below the surface 14, as is represented in FIG. 4. The further the measuring plane 32 is away from the surface 14, the greater the unsharpness becomes and the smaller the differences in brightness between the individual image points $Y_N$ become, N being the number of image points which are read out for the evaluation, still to be explained below, in a measuring field 36. The further the measuring plane 32 is away from the surface 14, the unsharper the recorded image becomes and the smaller the differences in brightness between the respectively neighbouring image points become. Seen from the converse viewpoint, this means that, when the measuring plane 32 is arranged in the surface 14, the differences in brightness are at the greatest and this maximum stands on the one hand for the focusing of the image and on the other hand, by the correlation with the position of the surface 14, for an exact distance 26.

Consequently, all the image points are read out and a function value F is determined in accordance with the following equation: $F=\Sigma(y_i-y_{right\ neighbour})^2+\Sigma(y_i-y_{upper\ neighbour})^2$, where $y_i$ is the brightness value of an image point. This is compared for example with a right neighbour on the one hand and an upper neighbour on the other hand. It may similarly be provided that, instead of the right neighbour, the left neighbour is chosen and, instead of the upper neighbour, the lower neighbour is chosen. Consequently, the sum of the differences in brightness can be ascertained by the function value F.

Figure 5:
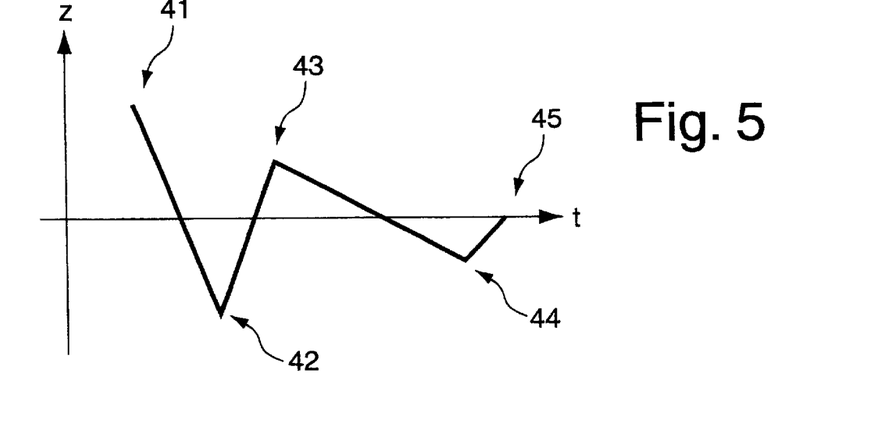
FIG. 5 shows a schematic representation of successive method steps for setting the distance between the collimator and the surface of the object of measurement.

In a first exemplary embodiment of the method, it is provided that a position of the surface 14 with respect to the Z axis is recorded. It follows from this that the function value F is changing, from which it follows that $F=f(Z)$. This results in a first embodiment for carrying out the method of setting a point of impingement of an X-radiation on an object of measurement. In the case of this embodiment, the Z coordinate along which the X-ray beam runs is taken into consideration as a further characteristic variable. The method of recording the point of impingement of an X-radiation on an object of measurement with a defined distance 26 between the collimator 17 and the surface 14 can take place in the following way:

The table 28 with the object of measurement 16 is transferred into a position in which the measuring plane 32 lies above the surface 14 of the object of measurement 16. This starting position 41 is represented in FIG. 5. Then the table 28 is moved along the Z coordinate towards the collimator 17, until a first intermediate position 42 is reached, which corresponds for example to a position according to FIG. 4. The absolute amount of the path is freely selectable. However, it has a minimum path of movement, in order that the exact distance 26 between the collimator 17 and the surface 14 is passed through with certainty. The speed of movement may take place relatively quickly in a first method step, which takes the form of an approximate search. Between the starting position 41 and the first intermediate position 42, individual measurements are advantageously carried out continuously, the individual measurement being ascertained from, for example, two or more individual values within a defined interval, so that the individual measurement comprises an average value of a number of individual values. These individual measurements of the images are evaluated in a way corresponding to the function F. After running through the approximate search, a maximum is ascertained by calculating the zero crossing of the first derivative as an approximation by interpolation. This first maximum is stored. Subsequently, the table 28 is transferred into a second intermediate position 43, from where a precision search takes place up to the third intermediate position 44. The travelling speed of the table 28 for the precision search is much slower than in the case of the approximate search. Individual measurements of the images are in turn carried out and evaluated in a way according to the method of the approximate search. Furthermore, the maximum is again ascertained. On the basis of the recording of the Z coordinate, the position 44 of the table is then known. Similarly, the Z coordinate of the maximum of the precision search is known and is advantageously compared with the approximate search. Subsequently, the table 28 is transferred from the second position 44 directly into a position 45, whereby the exact distance 26 between the surface 14 of the object of measurement 16 and the collimator 17 has been set.

The advantage of this procedure, in which the approximate search and the precision search have an identical direction of movement of the table 28, is a higher degree of accuracy of the ascertainment of the maximum and consequently of the exact distance 26. Similarly, the approximation to the maximum can likewise have the same direction of movement as that of the approximate search and precision search.

Figure 6:
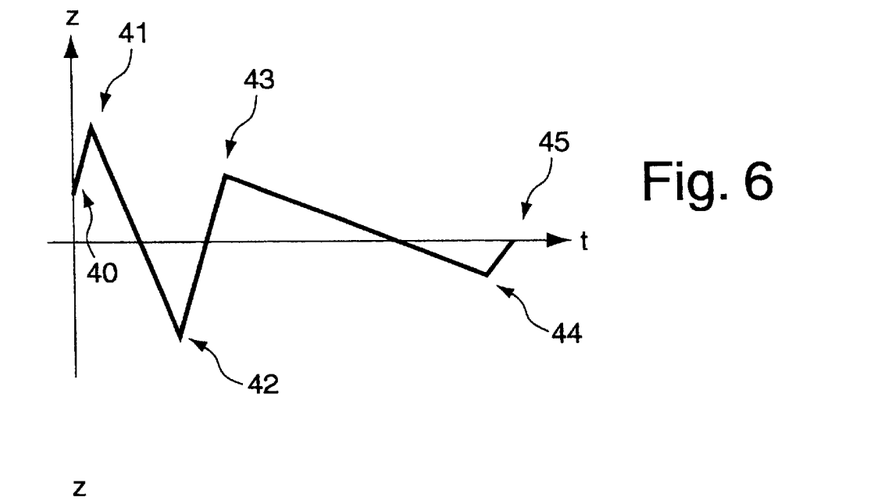
FIG. 6 shows a schematic representation of an alternative sequence of method steps according to FIG. 5

A further alternative way of carrying out the method is represented in FIG. 6. Before the commencement of the measurement, a first path of movement between a starting point 40 and the starting position 41 is covered. By reducing the difference in brightness of the image points between the points 40 and 41 on account of the unsharpness becoming greater, it is ensured that the table 28 is moved away from the collimator 17. In this way, it can at the same time be ensured that the table 28 does not run against the collimator 17, as long as the absolute amount of the unsharpness becomes greater. Following this, the method steps with respect to FIG. 5 can be carried out.

A further alternative refinement of the method of setting a point of impingement of an X-radiation to a specific distance 26 between the collimator 17 and the surface 14 of the object of measurement 16 is described in more detail below and explained by way of example on the basis of FIG. 7:

The approximate search and precision search, as described in FIGS. 5 and 6, and also a reverse movement from a first intermediate position 42 into a second intermediate position 43 take place by analogy with the embodiment of the method according to FIGS. 5 and 6. The present method takes place without the assignment of the function value F to a Z coordinate. After the approximate search between the starting position 41 and the first intermediate position 42, a rapid resetting takes place into the second intermediate position 43. Subsequently, a precision search takes place; during this, the function value F with the maximum of the function value F is compared with that of the approximate search. Once the maximum of the function value F is reached during the precision search, which corresponds substantially to the approximate search, the precision search is then stopped. As a result, the surface 14 has again been positioned with respect to the collimator 17 at the distance 26. Stopping of the table 28 may also take place if the maximum is slightly exceeded, in order to ensure that no unsharpnesses are interpreted as a maximum.

A further alternative of FIGS. 5 and 6 may consist in that the approximate search begins at the first intermediate position 42 and is carried out up to the second position 43. Subsequently, the precision search takes place up to the intermediate position 44 and the positioning to point 45.

Figure 7:
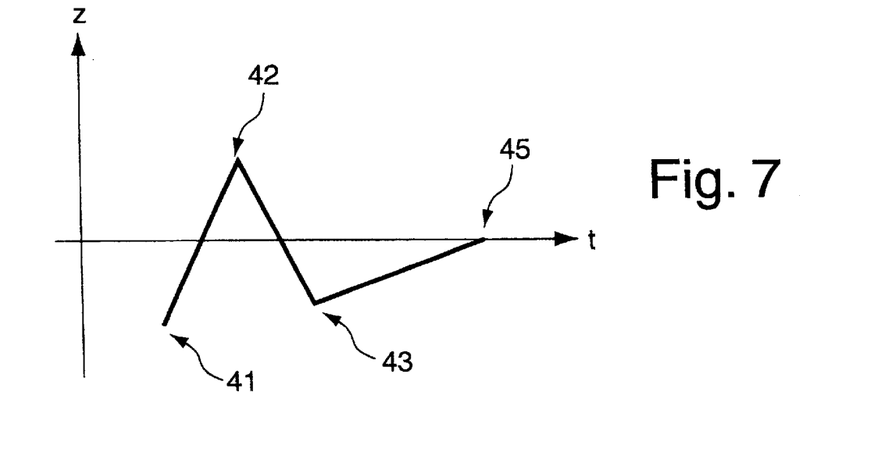
FIG. 7 shows a schematic representation of the sequence of a further alternative method of setting a point of impingement of an X-radiation on an object of measurement.

All the abovementioned embodiments of the method according to FIGS. 5 to 7 share the common feature that the approximate search and/or precision search can be repeated one or more times, it also being possible for the speed of movement and number of measurements during an approximate search and a precision search to be varied. The more often a search for the maximum is carried out, the more exactly the distance 26 from the collimator 17 can be set. Depending on the accuracy requirements, consequently one or more method steps can be strung together in order to increase the accuracy still further, with an increase in the time taken before the surface 14 of the object of measurement 16 is positioned in a final position with the exact distance 26 from the collimator 17.

For the evaluation of the image points of an image, an area 36 which is at least the size of the point of impingement of an X-radiation is advantageously chosen. The size of the image may optionally be set. Similarly, this evaluation of the optional image points may take place if the surface has been zoomed or made visible in an enlarged projection on a monitor.

The more differentiated the image areas are chosen to be for the evaluation of the difference in brightness of the image points, the more certainly setting can be made to the correct distance 26.

Furthermore, it may advantageously be provided that the abovementioned method of ascertaining a maximum with respect to the difference in brightness of the image points in an area is developed in such a way that an orientation of the surface 14 is recorded. For this purpose, it is advantageously provided that the area 36 is subdivided into four individual fields 51, 52, 53, 54, for example according to FIG. 8, the maximum of the difference in brightness for each field being ascertained separately.

An optimum alignment of the surface 14 is obtained when the measuring plane 32 of the surface 14 is aligned orthogonally with respect to the Z coordinate. A Z value is assigned for each field by a comparison, of for example fields 51, 52, 53, 54 according to FIG. 8, or their maximum, by the first derivative. If these values are the same within a certain error tolerance, it is concluded that the orientation is virtually ideal, i.e. perpendicular with respect to the optical axis of the viewing optics of the display device 21 or with respect to the X-ray beam. This can be monitored for example by standard deviations of the Z values.

Figure 8:
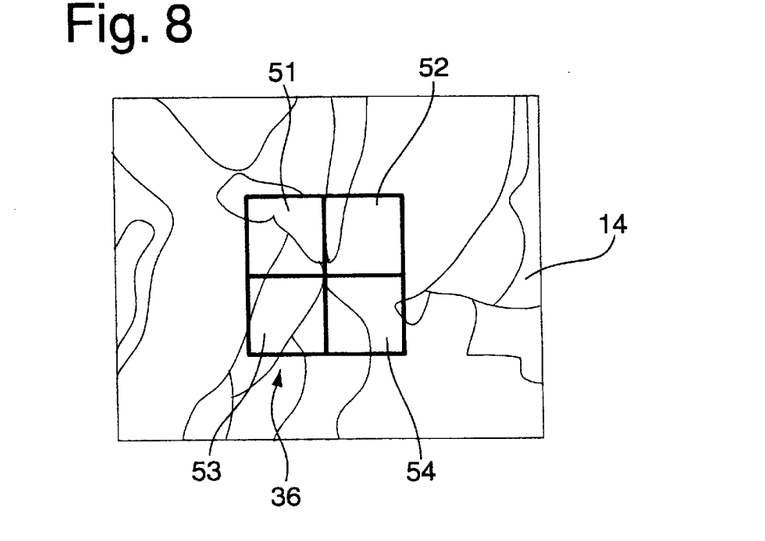
FIGS. 8 and 9 show a schematic representation of an image of an individual measurement with a measuring field divided into, for example, four individual fields, for ascertaining the orientation.

The characterization of the tilting or ascertainment of the orientation with regard to the deviation from the ideal measuring plane may take place for example by a coefficient $K_1$ being formed between the right and left fields 51, 53, 52, 54 in accordance with the equation $K_1=(z51'+z53')/(z52'+z54')-1$, and a coefficient $K_2$ between the upper and lower fields 51, 52, 53, 54, whereby the equation $K_2=(z51'+z52')/(z53'+z54')-1$ is formed. The tilting of the surface of the object of measurement can be ascertained by the test in accordance with $(K1)^2+(K2)^2<C$. A constant C is provided here, ascertained empirically in advance for an ideal plane and an aligned specimen in accordance with the formula $X=(K1)^2+(K2)^2$. This may comprise series of measurements, for example 5, 10, 15 or 20 measurements. The constant C is then intended to be, for example, three times the average value of X. Once the conditions are satisfied, the focusing to an average value $(z51'+z52'+z53'+z54')/4$ can take place.

Alternatively, it may be provided that, by reading out the individual image values within the fields 51, 52, 53, 54, the degree of tilting is ascertained in order thereafter to adjust a tilting table which has, for example, two degrees of freedom of movement, so that the surface can be positioned orthogonally with respect to the Z coordinate.

Figure 9:
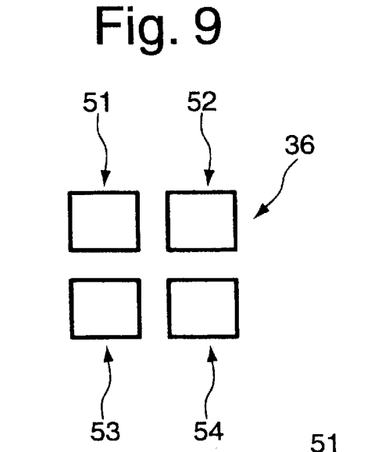

An alternative embodiment to FIG. 8 is represented in FIG. 9. Similarly, a number of fields 51, 52, 53, 54 may be provided in rows and columns, in order to record larger planar measuring fields 36 with respect to their tilting by an individual measurement.

Figure 10:
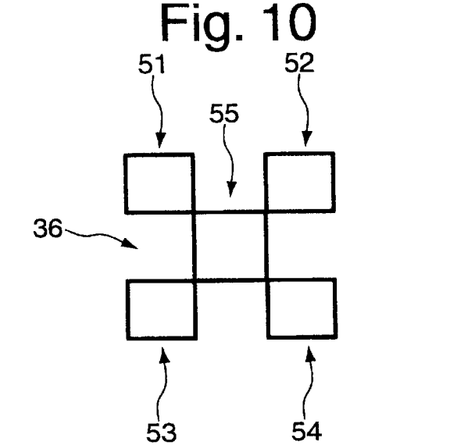
FIGS. 10 and 11 show a schematic representation of an alternative arrangement of individual fields within an image for ascertaining the orientation in the case of convex or concave surfaces.
Figure 11:
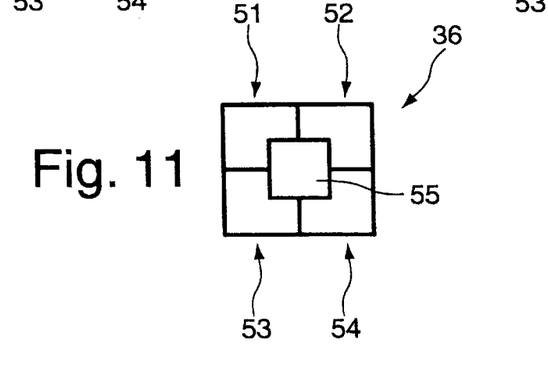

Further alternative arrangements of fields 51, 52, 53, 54, 55 for the reading out of an image of an individual measurement are represented in FIGS. 10 and 11. These arrangements are advantageously provided for the recording of convexly or concavely curved surfaces. A focusing of the image advantageously takes place on the basis of the derivative of the z55 value of the central field 55. The tilting can be monitored by analogy with the fields 51, 52, 53, 54 described in FIGS. 8 and 9. Further combinations and arrangements of the fields for ascertaining the orientation and the shape of surfaces can similarly be provided.

What is claimed is:

1. A method of setting a position of an object of measurement in layer thickness measurement by X-ray fluorescence in which a beam of an optical recording device is projected into a beam of X-radiation and in which a surface of the object of measurement is recorded and output as an image comprising a number of image points, comprising the steps of:

changing the distance between the surface and a collimator by an absolute amount of a path of movement, recording changes in brightness of image points in at least one measuring plane during at least one change of the distance between the surface and the collimator, ascertaining the maximum of the difference in brightness of the image points of an image after the at least one change of the distance, and setting the distance between the collimator and the surface of the object of measurement to the position of the ascertained maximum of the difference in brightness.

2. A method of setting a position of a object of measurement in layer thickness measurement by X-ray fluorescence in which a beam of an optical recording device is projected into the beam of the X-radiation, and in which a surface of the object of measurement is recorded and output as an image comprising a number of image points, comprising the steps of:

changing the distance between the surface and a collimator by an absolute amount of a path of movement, recording changes in brightness of image points in at least one measuring plane during at least one change of the distance between the surface and the collimator, ascertaining the maximum of the difference in brightness of the image points of an image after the at least one change of the distance, and choosing a direction opposite to the recording of the change in brightness for the changing of the distance, and stopping the changing of the distance immediately after the maximum of the difference in brightness is reached.

3. The method according to claim 1, wherein individual measurements for ascertaining changes in brightness of the image points of an image are carried out during changing of the distance between the collimator and the surface.

4. The method according to claim 1, wherein, for ascertaining the maximum value of the difference in brightness in a measuring plane, the image points are determined in a differential method according to the function $F=\Sigma(y_i-y_{right\ neighbour})^2+\Sigma(y_i-y_{upper\ neighbour})^2$, where $y_i$ is the brightness value of the image points.

5. The method according to claim 1, wherein the changing of the distance between the collimator and the surface of the object of measurement corresponds to an absolute amount of the measuring path in which at least the focal point lying at the distance from the collimator is passed through.

6. The method according to claim 1, wherein the individual measurement is ascertained from a number of individual images and an average value is formed from the values of the individual images.

7. The method according to claim 1, wherein during the individual measurement the speed for the changing of the distance between the collimator and the surface of the object of measurement is kept constant.

8. The method according to claim 1, wherein the changing of the distance in an approximate search for a first ascertainment of a maximum of the difference in brightness is carried out at an increased speed.

9. The method according to claim 1, wherein the distance between the collimator and the surface is reset after a first intermediate position at a resetting speed to a second intermediate position, which is preferably close to the starting position.

10. The method according to claim 1, wherein the return speed is set equal to or greater than that of the approximate search.

11. The method according to claim 1, wherein the precision search is carried out at a speed reduced in comparison with the approximate search.

12. The method according to claim 1, wherein, after passing through a focal point between the collimator and the surface of the object of measurement, the precision search is stopped and the surface of the object of measurement is set to the Z coordinate assigned to the maximum.

13. The method according to claim 1, wherein, before a commencement of the approximate search, a preset distance between the collimator and the surface of the object of measurement is increased.

14. The method according to claim 1, wherein the changing of the distance between the collimator and the surface takes place along a Z coordinate and the individual measurement of an image is assigned to a point in time of a corresponding Z coordinate.

15. The method according to claim 2, wherein, during the precision search, a comparison with the ascertained maximum value of the approximate search is carried out, and wherein, when there is a minimum in the difference of the maximum values, the changing of the distance between the collimator and the surface of the object of measurement is stopped.

16. The method according to claim 1, wherein the image points recorded in an image are recorded separately for ascertaining the difference in brightness individual fields.

17. The method according to claim 16, wherein a value of the maximum change in brightness is recorded for each field.

18. The method according to claim 16, wherein at least a division into four fields is chosen and, for the characterization of a tilting, the coefficient $K_1=(z51'+z53')/(z52'+z54')-1$ and the coefficient $K_2=(z51'+z52')/(z53'+z54')-1$ of individual fields are formed.

19. The method according to claim 16, wherein the coefficients $K_1$ and $K_2$ are evaluated in accordance with the formula $(K1)^2+(K^2)^2<C$.

20. The method according to claim 19, wherein the constant is ascertained by measurements of a reference surface.

21. The method according to claim 16, wherein the difference in brightness within each field is recorded and compared with the neighbouring field and wherein the angular deviation is converted into coordinates by which a tilting table receiving the object of measurement is activated.

22. The method according to claim 16, wherein, for ascertaining the orientation of convexly or concavely curved surfaces of objects of measurement, a central field and four fields assigned to the side edges or the corners are provided, the central field being evaluated for setting the distance and the at least four adjoining fields being evaluated for ascertaining the tilting.

23. The method according to claim 6, wherein the individual measurement is ascertained from a number of images at a freely selectable time interval.

* * * * *